United States Patent [19]

Ruud

[11] 4,042,825
[45] Aug. 16, 1977

[54] STRESSED-UNSTRESSED STANDARD FOR X-RAY STRESS ANALYSIS AND METHOD OF MAKING SAME

[75] Inventor: Clayton O. Ruud, Englewood, Colo.

[73] Assignee: Colorado Seminary, Denver, Colo.

[21] Appl. No.: 703,845

[22] Filed: July 9, 1976

[51] Int. Cl.² .......................................... G01N 23/20
[52] U.S. Cl. .................................. 250/272; 250/273; 250/277 CH
[58] Field of Search ............... 250/272, 273, 274, 275, 250/277 CH

[56] References Cited

U.S. PATENT DOCUMENTS 3,934,138   1/1976   Bens ...................................... 250/272

Primary Examiner—Craig E. Church
Attorney, Agent, or Firm—Edwin L. Spangler, Jr.

[57] ABSTRACT

This invention relates to a method and apparatus for simultaneously determining the sample to detector distance ($R_o$) and the angle between the surface normal and the incident X-ray beam ($\beta$) of a position sensitive X-ray detection device for use in stress analysis determinations on an unknown sample. More specifically, the apparatus comprises a stressable sheet, means capable of being detachably fastened to opposite ends of the sheet, spreader means interposed between the means fastened to opposite ends of the sheet operative upon actuation to spread said means apart and tension the sheet, and a strain-free film coating one surface of the sheet. The method comprises the steps of stretching a sheet of stressable material to a known tension, coating the sheet with a strain-free film, and thereafter determining both the sample to detector distance and the angle between the surface normal and the incident X-ray beam from said stressed-unstressed standard using the same set-up under which the stress measurements will be taken on the actual sample.

6 Claims, 5 Drawing Figures

U.S. Patent    Aug. 16, 1977    4,042,825
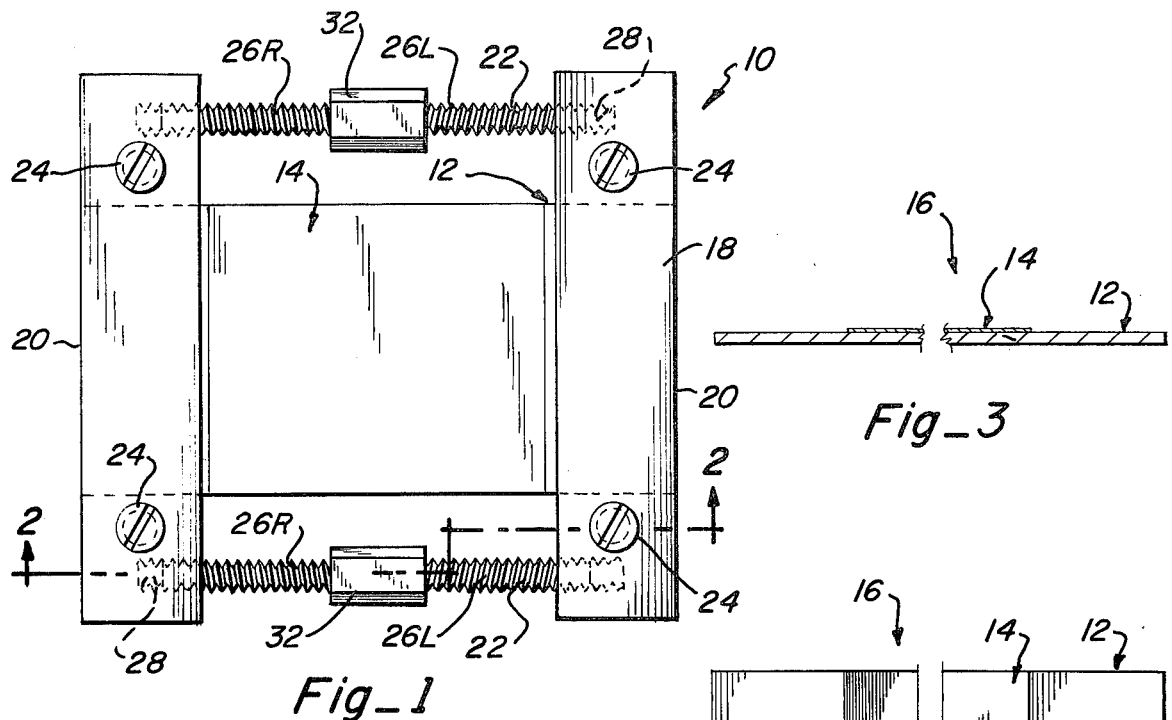
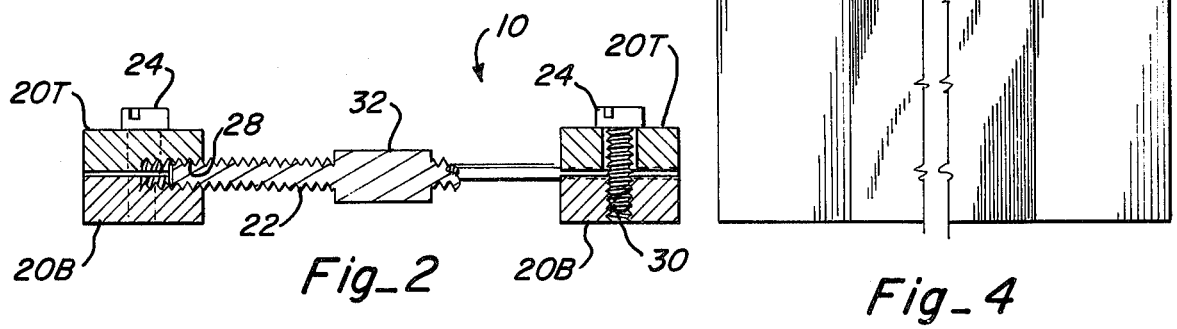
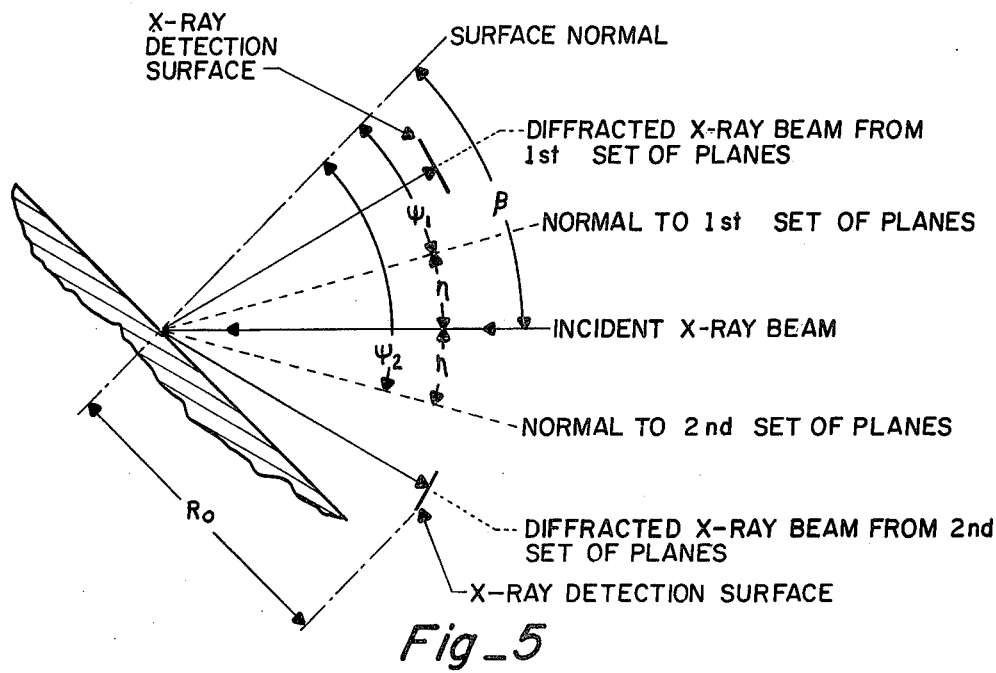

STRESSED-UNSTRESSED STANDARD FOR X-RAY STRESS ANALYSIS AND METHOD OF MAKING SAME

In the determination of residual stresses present in a sample to be analyzed, the technique of X-ray diffraction is one well-known technique employed to measure the lattice strains that exist between certain specially positioned planes. Equipment used for this purpose consists of either an X-ray diffractometer or an X-ray stress camera. Up until the relatively recent advent of instruments such as position-sensitive proportional counters, scintillation devices, etc., which eliminate the need for certain "scan" readings, a complex piece of equipment known as "scanning goniometer" had to be used to obtain readings rapidly and with good accuracy. Now, however, accurate and very rapid readings can be made by combining the camera geometry with position-sensitive devices other than the scanning goniometer.

Modern day X-ray diffraction equipment with position-sensitive detectors is capable of providing stress readings of considerable accuracy provided only that certain background information is obtained with a comparable degree of accuracy. Of this background information, certainly two of the most difficult values to obtain quickly and accurately are the sample to detector distance ($R_o$) and the angle between the so-called "surface normal" and the incident X-ray beam ($\beta$) for each new position of the sample, X-ray source and/or position-sensitive X-ray detector. X-ray film camera method diffractometers have relied upon these measurements being made mechanically with templates, scales of one type or another, protractors and the like; however, such methods are by far too inaccurate and time consuming to be consistent with the capabilities of the "new generation" position-sensitive X-ray detection devices. Accordingly, some better means had to be found for quickly and accurately determining these critical background constants and parameters.

A partial solution to the problem was found when it was discovered that with film techniques a stress-free material capable of providing a suitable diffracted X-ray peak with respect to sharpness, so-called "Bragg angle" and intensity could be coated upon the sample being tested at the exact spot where the stress reading was to be made. Then, if the set-up were the same as would be used in taking the stress readings from the unknown sample, it was possible to determine the critical sample to film distance from the reading taken from the strain-free coating. Usually, a crystalline powder was used and petroleum jelly or the like employed for the purpose of adhering the powder to the surface of the sample.

Unfortunately, the foregoing technique only resulted in a determination of the sample to detector distance and gave no information whatsoever concerning the equally critical angle between the surface normal and the incident X-ray beam. As previously noted, this critical bit of information has, heretofore, been obtained manually with a hand-held protractor or the like being used to determine the angle between the incident X-ray beam and the surface normal of the actual unknown sample being analyzed.

It has now been found in accordance with the teaching of the present invention that both of these critical background values can be determined by the simple, yet unobvious, expedient of placing a stressable sheet under a known tension, coating the sheet thus stressed with a film of unstressed material and taking readings on both the position and attitude of the incident X-ray beam with respect to the surface of this known sample using the selfsame geometry under which the ultimate stress analysis will be conducted upon the unknown sample.

It is, therefore, the principal object of the present invention to provide a novel and improved method for rapidly and accurately determining both the position and attitude of an incident X-ray beam relative to an unknown sample being stress analyzed.

A second objective is the provision of a novel stressed-unstressed sample for use in carrying out the aforementioned method.

Another objective of the invention forming the subject matter hereof is the provision of a method for determining two key values necessary in X-ray stress analysis from a single simple set-up.

Still another object is to provide a known sample which, when used in accordance with the claimed method, provides critical information heretofore obtainable only by mechanical measurement or through use of pre-positioned sample holders.

An additional object is to provide means for stressing a stressable sheet material preparatory to or after coating same with an unstressed film so as to not interfere with the latter operation.

Further objects are to provide a stressed-unstressed specimen for X-ray stress analysis which is simple, inexpensive, versatile, reliable, accurate, easy to use, compact and ideally suited for use with the latest in position-sensitive X-ray detection devices.

Other objects will be in part apparent and in part pointed out specifically hereinafter in connection with the description of the drawings that follows, and in which:

FIG. 1 is a top plan view showing the entire assembly which comprises the stressed-unstressed standard mounted and held within the jaws of the clamp frame;

FIG. 2 is a section taken along line 2—2 of FIG. 1;

FIG. 3 is a fragmentary longitudinal section of the stressed-unstressed sample subassembly, the central portion of which has been broken away to conserve space;

FIG. 4 is a fragmentary top plan view of the sample subassembly of FIG. 3, also having the central portion thereof broken away to conserve space; and, FIG. 5 is a diagram illustrating the various angular relationships between the incident X-ray beam, the diffracted beams from the first and second planes of the sample and the positions of the X-ray detection surface relative to the latter when determining the foregoing angular relationships.

Referring next to the drawings for a detailed description of the present invention, reference numeral 10 has been chosen to broadly designate the stressed-unstressed standard which includes a sheet of stressable material 12 coated on one surface with a film of unstressed material 14 to produce a subassembly designated in a general way by numeral 16 which is, in turn, clamped and maintained in a stressed condition within an adjustable clamp frame that has been broadly identified by numeral 18. In the particular form illustrated, the stressable material 12 comprises a rather small rectangular sheet of sheet metal such as aluminum, the length of which need not be more than about a quarter of an inch or so. The unstressed film 14, on the other hand, consists as it has in the past of a strain-free material, usually a crystalline powder, which gives a suitable diffracted X-ray peak with respect to sharpness, Bragg angle and intensity. In the past, petroleum jelly or the like has been employed to adhere the strain-free crystalline powder to the surface of the unknown being analyzed at the precise spot where the stress reading is to be made and after the X-ray detection device has been set to take the necessary readings. In accordance with the teaching of the present invention, on the other hand, no attempt is made to localize the crystalline powder to that area of the unknown where the stress will be measured, but instead, more or less the whole surface of the stressable sheet is coated therewith, preferably by using the well-known vacuum evaporative technique instead of an adhesive of some sort. The stressable sheet 12 is preferably pre-tensioned before the film of unstressed material 14 is deposited upon the surface thereof so as to eliminate any possibility that mechanical inneraction between the particles of the unstressed film could result in a stressed condition existing therein. Silver particles comprise one well-known type of unstressed crystalline substance that can be vacuum-evaporated onto the surface of the stressable sheet and provide good results in the determination of the sample to detector distance $R_o$.

The adjustable clamp frame 18 comprises in the particular form shown a pair of clamp subassemblies 20 detachably secured to opposite ends of the stressed-unstressed sheet subassembly 16 in essentially-spaced parallel relation to one another and a pair of spreader elements 22 interconnecting corresponding ends of these clamp subassemblies. These spreaders are operative upon actuation to move the clamp subassemblies apart and place the stressable plate 12 secured therein under tension without, of course, stressing the unstressed film 14. Specifically, each clamp subassembly 20 comprises, in the particular form shown, a pair of metal jaws 20T and 20B detachably held in clamped relation on the top and bottom of plate 12 along one end thereof by a pair of screw elements 24, the construction and function of which will be described presently.

Spreader elements 22, as illustrated, comprise a pair of screws bridging the gap between the clamp subassemblies and threaded into the latter when in tightly clamped relation on the assembly 18. The threads 26R and 26L on opposite ends of each screw are of the opposite hand in the manner of a toggle bolt so that actuation of the screw in one direction will spread the clamp subassemblies 20 apart and actuation in the opposite direction will bring them together. The internally-threaded sockets 28 in the mating jaws of each clamp subassembly are, of course, of the same hand as the threaded section of the screw received therein.

The bottom jaw 20B of each clamp subassembly 20 includes an internally-threaded opening 30 into which screws 24 thread. Actuation of these screws 24, of course, moves the jaws toward and away from one another in the manner of a conventional vise.

Each spreader 22 is shown provided with means 32 for rotating same. In the particular form illustrated, such means comprises a nut although knurled knobs or even an opening through the shaft defined thereby for the reception of a pin would function just as well.

Now, when using so-called "single" exposure technique for calculating stress, the equation used is as follows:

$$\sigma\phi = (\frac{E}{1+v}) \frac{\cot \theta_o (S_2 - S_1)}{2 R_o [\sin^2 (\beta + \eta) - \sin^2 (\beta - \eta)]} \quad (1)$$

where $\sigma\phi$ = the stress at some angle $\phi$ to a reference direction in the plane of the surface of the sample in which that stress is being measured $E$ = elastic modulus $v$ = Poisson's ratio $\theta$ = Bragg angle of X-ray incidence to the atomic planes used for X-ray diffraction in an unstressed material $S_1$ = the position of the diffracted X-ray peak between the incident beam and the sample surface normal $S_2$ = the position of the diffracted X-ray peak between the incident beam and the plane of the surface $\eta = 90 - \theta_o$ $S_1$ and $S_2$ are measured quantities for the stress determination whereas the other parameters must be known. The values of $R_o$ and $\beta$ change, usually with each stress reading. In the event planar or straight line X-ray sensors located in perpendicular relation to the incident beam are used in place of sensors having a curvature consistent with $R_o$, then the quantity "$\sec^2 2\theta$" must be inserted in the denominator of equation (1).

In accordance with the teaching of the instant invention, the pretensioned plate 12 coated with an unstressed film 14 is placed over the exact position at which the stress is ultimately to be measured. Next, the value of $R_o$ is obtained as in the past from the known Bragg angle of the strain-free material 14 and the values of $S_1$ and $S_2$ for the stressed-unstressed standard obtained from the X-ray detection device. Here, however, the technique differs because the prestressed standard 12 upon which the strain-free material is coated is used to determine the unknown angle $\beta$ in equation (1). This can be done simultaneously with the determination of $R_o$ because the prestressed standard has a known $\sigma\phi$ and the determination of the position of diffracted X-ray peaks $S_1$ and $S_2$ for the stressed-unstressed standard can easily and rapidly be made with the position sensitive detector device instead of some inaccurate mechanical tool like a protractor.

Once the $S_1$ and $S_2$ for the stressed-unstressed standard parameters are determined along with $R_o$, these values can be substituted in the following equation:

$$\sin^2\Psi_x = (\frac{E}{1+v}) \frac{\cot \theta_o}{2 R_o \sigma\phi} (S_x - S_o) \quad (2)$$

where $\psi_x = \psi_1$ or $\psi_2$ depending upon whether $S_1$ or $S_2$ is used. Equation (2) is actually a re-arrangement of the prior art double exposure technique equation found in the SAE Handbook Supplement, "Residual Stress Measurement by X-ray Diffraction—SAE J784a", Soc. of Auto. Engn., Inc., Two Pennsylvania Plaza, N.Y., N.Y., 10001, 1971. $\beta$ can be calculated from either the $\psi_1$ or $\psi_2$ values using the relation which follows:

$$\beta = \psi_1 + \eta = \psi_2 - \eta$$

Actually, $\beta$ should be calculated from $S_1$ and $S_2$ and averaged to find the parameter used in the determination of the unknown stress. Again this equation assumes a curved X-ray sensing surface with radius $R_o$ and the term $\sec^2 2\theta$ must be placed in the denominator when a flat or planar sensing surface is used.

Finally, reference is made to the diagram of FIG. 5 wherein the various terms found in the foregoing equations have been shown in their relation to the first and second sets of planes of the sample and the positions of the X-ray detection surface in determining these values.

What is claimed is:

1. Apparatus for use with a position-sensitive X-ray detection device in the determination of the sample to detector distance and the angle between the surface normal and the incident X-ray beam preparatory to analyzing the stresses within an unknown sample which comprises: a sheet of stressable material; a film of strain-free material coated upon the stressable sheet; means detachably fastened to the stressable sheet in opposed spaced relation to one another; and means interposed between said opposed means operative upon actuation to change the spacing therebetween and place the stressable sheet under stress without stressing the strain-free film coated thereon.

2. The apparatus of claim 1 wherein the opposed means comprise clamp members having opposed jaws and means interconnecting said jaws for closing same upon a workpiece.

3. The apparatus as set forth in claim 1 in which the means interposed between the opposed means comprise spaced substantially parallel threaded elements having threads a different hand on opposite ends thereof; and, in which opposed portions of said opposed means include aligned internally-threaded sockets for receiving the threads on the adjacent ends of the threaded elements.

4. The apparatus as set forth in claim 3 in which means are located intermediate the ends of each threaded element for turning same.

5. The improved method for determining the sample to detector distance and the angle between the surface normal and the incident X-ray beam of a position-sensitive X-ray detection device preparatory to determining the stress within an unknown sample which comprises the steps of: loading a sheet of stressable material to place same under stress, coating the stressable material thus stressed with a film of strain-free material and determining the sample to detector distance and the angle between the surface normal and the incident X-ray beam with respect to said sheet thus pretensioned and coated with it positioned in the same location relative to said detector that the unknown sample will occupy when making the stress measurements thereon.

6. The improved method as set forth in claim 5 in which the strain-free film is vacuum-deposited upon the surface of the pre-stressed sheet.

* * * * *